(12) United States Patent
Song et al.

(10) Patent No.: US 11,596,379 B2
(45) Date of Patent: Mar. 7, 2023

(54) ULTRASOUND TREATMENT DEVICE FOR HIFU AND ULTRASOUND IMAGE, AND CONTROL METHOD THEREFOR

(71) Applicant: SOGANG UNIVERSITY RESEARCH FOUNDATION, Seoul (KR)

(72) Inventors: Tai-Kyong Song, Seoul (KR); Hyungil Kang, Daejeon (KR); Sua Bae, Seoul (KR); Ji Won Park, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 186 days.

(21) Appl. No.: 16/073,970

(22) PCT Filed: Dec. 20, 2016

(86) PCT No.: PCT/KR2016/014948
§ 371 (c)(1),
(2) Date: Jul. 30, 2018

(87) PCT Pub. No.: WO2017/135567
PCT Pub. Date: Aug. 10, 2017

(65) Prior Publication Data
US 2019/0038253 A1    Feb. 7, 2019

(30) Foreign Application Priority Data

Feb. 1, 2016    (KR) .................. 10-2016-0012107

(51) Int. Cl.
*A61B 8/08*    (2006.01)
*A61B 18/08*    (2006.01)
(Continued)

(52) U.S. Cl.
CPC ............. *A61B 8/08* (2013.01); *A61B 8/00* (2013.01); *A61B 18/082* (2013.01); *A61N 7/00* (2013.01);
(Continued)

(58) Field of Classification Search
CPC .......... A61B 8/08; A61B 8/00; A61B 18/082; A61B 2090/378; A61N 7/02; A61N 7/00;
(Continued)

(56) References Cited

U.S. PATENT DOCUMENTS 4,069,467 A    1/1978    Burckhardt et al.
4,586,512 A    5/1986    Do-huu et al.
(Continued)

FOREIGN PATENT DOCUMENTS

DE    20200717913    3/2008
EP    2157666    2/2010
(Continued)

OTHER PUBLICATIONS

Goss et al., "Sparse Random Ultrasound Phased Array for Focal Surgery", IEEE Transactions on Ultrasonics, Ferroelectrics, and Frequency Control, vol. 43, No. 6, Nov. 1996, pp. 1111-1121. (Year: 1996).*
(Continued)

*Primary Examiner* — Joseph M Santos Rodriguez
*Assistant Examiner* — Kaitlyn E Sebastian
(74) *Attorney, Agent, or Firm* — Duane Morris LLP; Gregory M. Lefkowitz; Joaquin Hernandez

(57) ABSTRACT

The present invention relates to an ultrasound treatment device for HIFU and an ultrasound image, and to a control method therefor. The ultrasound treatment device comprises: a plurality of image converters disposed on one surface of a probe assembly to transmit ultrasound signals to a target and receive signals reflected by the target to create (Continued)

an ultrasound image; a plurality of high intensity focused ultrasound (HIFU) converters disposed on the surface of the probe assembly so as to be located in different positions from the image converters, wherein the HIFU converters transmit ultrasound signals to a target to generate heat energy, thereby treating a tissue within a focusing area; and a control unit performing control such that the difference between apertures of converter arrays constituted by the image converters and the HIFU converters, respectively, is less than a predetermined value.

20 Claims, 11 Drawing Sheets

(51) Int. Cl.
  *A61N 7/00* (2006.01)
  *A61B 8/00* (2006.01)
  *A61N 7/02* (2006.01)
  *B06B 1/02* (2006.01)
  *B06B 1/06* (2006.01)
  *A61B 90/00* (2016.01)

(52) U.S. Cl.
  CPC .............. *A61N 7/02* (2013.01); *B06B 1/0215* (2013.01); *A61B 2090/378* (2016.02); *A61N 2007/0004* (2013.01); *A61N 2007/0073* (2013.01); *A61N 2007/0078* (2013.01); *B06B 1/0622* (2013.01); *B06B 2201/76* (2013.01)

(58) Field of Classification Search
  CPC .... A61N 2007/0073; A61N 2007/0078; A61N 2007/0004; B06B 1/0215; B06B 1/0622; B06B 2201/76
  See application file for complete search history.

(56) References Cited

U.S. PATENT DOCUMENTS

| | | | | |
|---|---|---|---|---|
| 5,520,188 | A | | 5/1996 | Hennige et al. |
| 5,938,608 | A | | 8/1999 | Bieger et al. |
| 6,042,556 | A | * | 3/2000 | Beach ...................... A61N 7/02 600/437 |
| 2010/0076352 | A1 | * | 3/2010 | Kim .......................... A61N 7/02 601/2 |
| 2011/0130663 | A1 | * | 6/2011 | Raju ..................... B06B 1/0622 600/459 |
| 2012/0035464 | A1 | * | 2/2012 | Raju ........................ A61N 7/02 600/411 |
| 2013/0116561 | A1 | * | 5/2013 | Rothberg ................. A61B 8/13 600/438 |
| 2016/0007960 | A1 | * | 1/2016 | Son ...................... A61B 8/5207 601/3 |
| 2018/0264291 | A1 | * | 9/2018 | Rem-Bronneberg .... A61N 7/02 |

FOREIGN PATENT DOCUMENTS

| | | |
|---|---|---|
| JP | 2015029664 | 2/2016 |
| KR | 1009221800000 | 10/2009 |
| KR | 1020110074326 | 6/2011 |
| KR | 1020110127736 | 11/2011 |
| KR | 103173590000 | 10/2013 |
| KR | 1015334020000 | 6/2015 |
| WO | 2011092683 | 8/2011 |

OTHER PUBLICATIONS

Goss et al., "Sparse Random Ultrasound Phased Array for Focal Surgery", IEEE Transactions on Ultrasonics, Ferroelectrics, and Frequency Control, vol. 43, No. 6, Nov. 1996, pp. 1111-1121.

* cited by examiner

[A]        [B]

ULTRASOUND TREATMENT DEVICE FOR HIFU AND ULTRASOUND IMAGE, AND CONTROL METHOD THEREFOR

TECHNICAL FIELD

The present disclosure relates to ultrasound technology for noninvasive treatment based on medical image diagnosis, and more particularly, to an ultrasound treatment device in which an ultrasonic converter for obtaining an ultrasound image and an ultrasonic converter for treatment are implemented in one probe, and a method for controlling a plurality of ultrasonic converters provided in the ultrasound treatment device.

BACKGROUND ART

Ultrasound (US) imaging is the technique of imaging the structure and characteristics of a monitoring region in the human body by applying an ultrasonic signal to the monitoring region using an ultrasound probe, receiving the ultrasonic signal reflected back from the tissue and extracting information included in the signal. This has an advantage that real-time images harmless for the human body can be obtained at low costs, compared other medical imaging systems including X-ray, CT, MRI and PET.

It is known that human body tissues are necrotized when the temperature of the part is 60-85° C. Using this phenomenon, High Intensity Focused Ultrasound (HIFU) treatment is the technique of focusing ultrasound energy on one point (focal point) to necrotize the lesion tissue by heat (thermal coagulation) and mechanical energy (cavitation). With the development of ultrasound treatment, a specific ultrasound treatment, especially, HIFU, is applied to damaging dose to effectively treat many types of diseases, especially tumors. When comparing to the conventional surgery and chemotherapy, HIFU treatment causes less damage to patients and achieves non-invasive treatment. Accordingly, the clinical applications of HIFU are developed fast. The symptoms include liver cancer, bone sarcoma, breast cancer, pancreas cancer, kidney cancer, soft tissue tumor and pelvic tumor.

In general, an ultrasound tumor treatment device employs sphere focusing. Ultrasound emitted from all points is focused on the center of a sphere. The emitter on the ultrasound treatment device emits ultrasound from the outside of the body to the inside of the body, and the ultrasound is focused to form a high energy focal point during emission and transmission. Accordingly, high intensity and continuous ultrasound energy is applied to the patient's lesion region.

The effect of too high temperature (65-100° C.), the cavitation effect, the mechanical effect and the sonochemical effect generated from the focal point are used to selectively cause coagulative necrosis of the affected tissue, and prevent the proliferation, invasion and metastasis of tumor.

The accurate, safe and effective localization of the focal point is essential for successful treatment while applying HIFU treatment, and there is a need to further improve the convenience of operation for positioning the target. Accordingly, treatment may be performed through HIFU signals without damaging the important vessels and organs, and it is necessary to monitor accurate focusing of HIFU treatment signals to improve the stability and accuracy of HIFU treatment.

However, when high intensity ultrasound energy used for HIFU treatment is focused on an unwanted region, there is a problem that tissues other than the lesion part are necrotized, and accordingly there is a strong need for HIFU treatment technology in conjunction with ultrasound technology for imaging to obtain ultrasound images. The prior art document presented below introduces technical means for combining ultrasound imaging technology with HIFU treatment technology.

RELATED LITERATURE

Korean Patent Publication No. 10-2013-0034987, published Apr. 8, 2013, Industry-University Cooperation Foundation Sogang University

DISCLOSURE

Technical Problem

The embodiments of the present disclosure are intended to solve the problem that the conventional probe structure for performing high intensity focused ultrasound (HIFU) treatment through ultrasound image monitoring fails to realize a sufficiently large aperture of any one of converters for imaging and converters for HIFU treatment due to difficulties in placing the converters, resulting in low resolution of image, causing adverse effects to normal tissues, and overcome the limitation that the ultrasound treatment equipment reduces in the overall performance due to the frequency response characteristic that is not specialized for low frequency signals or high frequency signals in the probe structure using a general-purpose converter.

Technical Solution

To achieve the above-described technical object, an ultrasound treatment device according to an embodiment of the present disclosure includes a plurality of image converters configured to transmit ultrasound signals to a target and receive the signals reflected from the target to create an ultrasound image, a plurality of high intensity focused ultrasound (HIFU) converters configured to transmit ultrasound signals to the target to generate heat energy, thereby treating the tissue within a focusing area, and a control unit configured to perform control such that a difference in aperture of converter arrays constituted by the image converters and the HIFU converters, respectively, is within a predetermined value, wherein the image converters and the HIFU converters are each disposed in different positions on one surface of the probe assembly, and are formed to have frequency response characteristics of different center frequency bands.

In the ultrasound treatment device according to an embodiment, the HIFU converters have frequency response characteristic of lower center frequency band than the image converters. Additionally, preferably, the image converters have frequency response characteristic of a center frequency band of 3 MHz to 5 MHz, and the HIFU converters have frequency response characteristic of a center frequency band of 1 MHz to 1.5 MHz.

In the ultrasound treatment device according to an embodiment, the image converters and the HIFU converters may be each arranged randomly or in sparse array on one surface of the probe assembly.

In the ultrasound treatment device according to an embodiment, the image converters and the HIFU converters may form a circular image converter group and a circular HIFU converter group respectively by the same type of converter, and the circular image converter group and the circular HIFU converter group may be arranged to form concentric circles having different radii.

In the ultrasound treatment device according to an embodiment, the control unit may generate and apply ultrasonic signals of different center frequency bands to each of the image converters and the HIFU converters.

To achieve the above-described technical object, an ultrasound treatment device according to another embodiment of the present disclosure includes a plurality of image converters configured to transmit ultrasonic signals to a target and receive the signals reflected from the target to create an ultrasound image, and a plurality of HIFU converters configured to transmit ultrasonic signals to the target to generate heat energy, thereby treating the tissue within a focusing area, wherein the image converters and the HIFU converters form a circular image converter group and a circular HIFU converter group respectively by the same type of converter, and are arranged on one surface of the probe assembly to form concentric circles having different radii.

In the ultrasound treatment device according to another embodiment, the image converters included in the circular image converter group and the HIFU converters included in the circular HIFU converter group may be disposed at a location where the influence of grating lobe generated by a gap between the converters is minimized.

In the ultrasound treatment device according to another embodiment, the image converters included in the circular image converter group and the HIFU converters included in the circular HIFU converter group may be arranged at the same interval on each concentric circle.

In the ultrasound treatment device according to another embodiment, the circular image converter group and the circular HIFU converter group may be repeatedly arranged in an alternating manner in a direction in which the radius increases from a center of the probe assembly.

In the ultrasound treatment device according to another embodiment, the circular image converter group and the circular HIFU converter group may be arranged such that adjacent concentric circles have the same interval.

In the ultrasound treatment device according to another embodiment, the radii of at least two virtual concentric circles may be determined such that the area of each region separated by the virtual concentric circles is equal, a new concentric circle may be formed on the basis of an average of radii of adjacent virtual concentric circles of the virtual concentric circles, and any one of the circular image converter group and the circular HIFU converter group may be disposed on the formed new concentric circle.

In the ultrasound treatment device according to another embodiment, the radii of at least two virtual concentric circles may be determined such that the area of each region separated by the virtual concentric circles is equal, a new concentric circle may be formed at a location where the area of each region separated by the virtual concentric circles is divided into two, and any one of the circular image converter group and the circular HIFU converter group may be disposed on the formed new concentric circle.

To achieve the above-described technical object, a control method for an ultrasound treatment device according to still another embodiment of the present disclosure includes (a) transmitting ultrasonic signals to a target and receiving the signals reflected from the target to create an ultrasound image of a target tissue for treatment, using a plurality of image converters disposed on one surface of a probe assembly, (b) transmitting ultrasonic signals to the target to generate heat energy, thereby treating the tissue within a focusing area, using a plurality of HIFU converters disposed in different positions from the image converters on one surface of the probe assembly, and (c) transmitting ultrasonic signals to the target and receiving the signals reflected from the target to create an ultrasound image of the treated condition of the tissue, using the plurality of image converters, wherein the steps (b) and (c) are repeatedly performed at least once by controlling each of the image converters and the HIFU converters.

In the control method for an ultrasound treatment device according to still another embodiment, the image converters and the HIFU converters may be each arranged randomly or in sparse array on one surface of the probe assembly, and the steps (a) to (c) may include selectively driving each of the image converters and the HIFU converters, and determining the aperture of the converter array by the driven converters.

In the control method for an ultrasound treatment device according to still another embodiment, the image converters and the HIFU converters may form a circular image converter group and a circular HIFU converter group respectively by the same type of converter, and the circular image converter group and the circular HIFU converter group may be arranged to form concentric circles having different radii, and the steps (a) to (c) may include selectively driving each of the image converters and the HIFU converters, and determining the aperture of the converter array by the diameter of the driven converter group. Additionally, the steps (a) to (c) may include selectively driving converters arranged at the same interval on each concentric circle among the image converters included in the circular image converter group and the HIFU converters included in the circular HIFU converter group. Further, the steps (a) to (c) may include selectively driving the circular image converter group and the circular HIFU converter group repeatedly arranged in an alternating manner in a direction in which the radius increases from a center of the probe assembly, and performing control such that a difference in aperture of the driven converter group is within a predetermined value.

In the control method for an ultrasound treatment device according to still another embodiment, the steps (a) to (c) may include selectively driving each converter disposed at a location where the influence of grating lobe generated by a gap between the converters is minimized.

In the control method for an ultrasound treatment device according to still another embodiment, the HIFU converters may have frequency response characteristic of lower center frequency band than the image converters, and the steps (a) to (c) may include generating and applying ultrasonic signals of different center frequency bands to each of the image converters and the HIFU converters.

Advantageous Effects

The embodiments of the present disclosure may improve the lateral direction resolution with the large converter aperture by placing two types of converters for different purposes of uses at each separate position using the entire region of the probe, may focus energy on only a target local part for treatment without damaging normal tissues around the lesion part by using the placement technique for minimizing the influence of the grating lobe, and may simultaneously achieve effective high intensity focused ultrasound (HIFU) treatment using low band frequency and improved axial direction resolution using high band frequency by employing converters having suitable frequency response for each purpose.

DETAILED DESCRIPTION OF MAIN ELEMENTS 10, 210: Ultrasonic converter for imaging
20, 220: Ultrasonic converter for treatment
310: Ultrasonic converter capable of image acquisition and treatment
30: Control unit
50, 250, 350: Probe assembly

BEST MODE

An ultrasound treatment device according to an embodiment of the present disclosure includes a plurality of image converters configured to transmit ultrasound signals to a target and receive the signals reflected from the target to create an ultrasound image, a plurality of high intensity focused ultrasound (HIFU) converters configured to transmit ultrasound signals to the target to generate heat energy, thereby treating the tissue within a focusing area, and a control unit configured to perform control such that a difference in aperture of converter arrays constituted by the image converters and the HIFU converters, respectively, is within a predetermined value, wherein the image converters and the HIFU converters are each disposed in different positions on one surface of the probe assembly, and are formed to have frequency response characteristics of different center frequency bands.

MODE FOR INVENTION

Prior to describing the embodiments of the present disclosure, after introducing the physical feature of imaging and HIFU treatment based on ultrasound technology in brief, the technical means adopted by the embodiments of the present disclosure to overcome the substantial problem and limitation encountered when operating the two together will be presented next.

High intensity focused ultrasound (HIFU) is a noninvasive treatment technique by applying high intensity ultrasound irradiation to the human body tissue to necrotize the lesion tissue such as cancer within the human body tissue, and it involves converting an electrical signal to an ultrasonic signal using a plurality of converters arranged in a probe and transmitting the ultrasonic signal into the human body. In general, HIFU focuses and transmits a higher intensity ultrasonic signal to a target region for treatment than those used for ultrasound imaging, and performs operation many times to necrotize the lesion tissue. The irradiated energy is converted to heat energy and the tissue disposed at the focusing area of ultrasound is heated to high temperature and necrotized, and for accuracy and safety of treatment, there is a need to irradiating ultrasound for imaging onto the necrotized region and its surrounding before the start of treatment or during multiple HIFU irradiation to obtain an ultrasound image, and receive feedback of information associated with whether the tissue is necrotized and the surrounding tissues are damaged.

Figure 1:
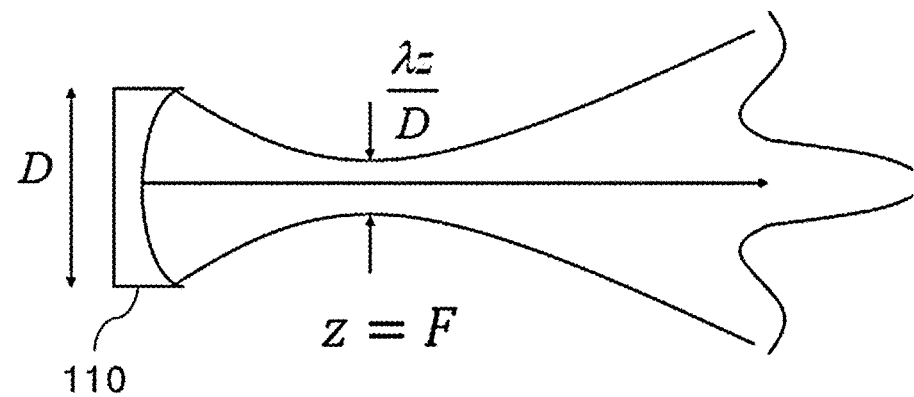
FIG. 1 is a diagram illustrating the feature of ultrasound imaging and ultrasound treatment according to the aperture of a converter.

FIG. 1 is a diagram illustrating the feature of ultrasound imaging and ultrasound treatment according to the aperture of a converter, visually representing a focal point of an ultrasonic signal focused from an ultrasonic converter 110.

In general, ultrasound for ultrasound imaging is characterized in that when an ultrasonic signal is transmitted with higher frequency, an image of higher resolution can be obtained. Not only the converter for ultrasound image but also the converter for HIFU treatment needs an accurate focal point and localization for successful treatment, and the reason is because necrosis of normal tissues can be prevented through accurate focus monitoring.

Meanwhile, there is a physical feature that as the aperture of the ultrasonic converter is larger, a beam can be focused on a narrower area, and this feature is shown in FIG. 1. Referring to FIG. 1, D is the aperture of the ultrasonic converter 110, which is found inversely proportional to the beam width of the focal point. That is, the larger aperture of the converter 110, the higher resolution of the ultrasound image, and thus there are advantages that a high quality image can be obtained, and an operator can perform local treatment on only a desired part accurately in HIFU treatment.

Figure 2:
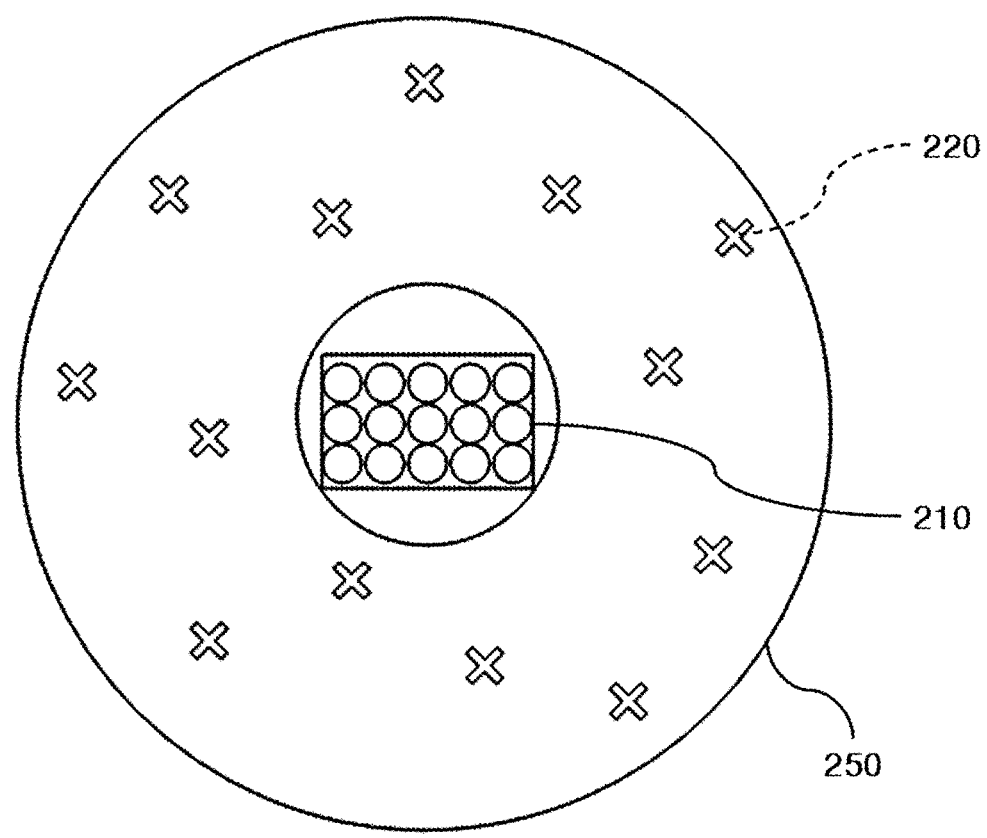
FIGS. 2 and 3 are diagrams showing a probe structure having both ultrasonic converters for obtaining an ultrasound image and high intensity focused ultrasound (HIFU) converters for ultrasound treatment.
Figure 3:
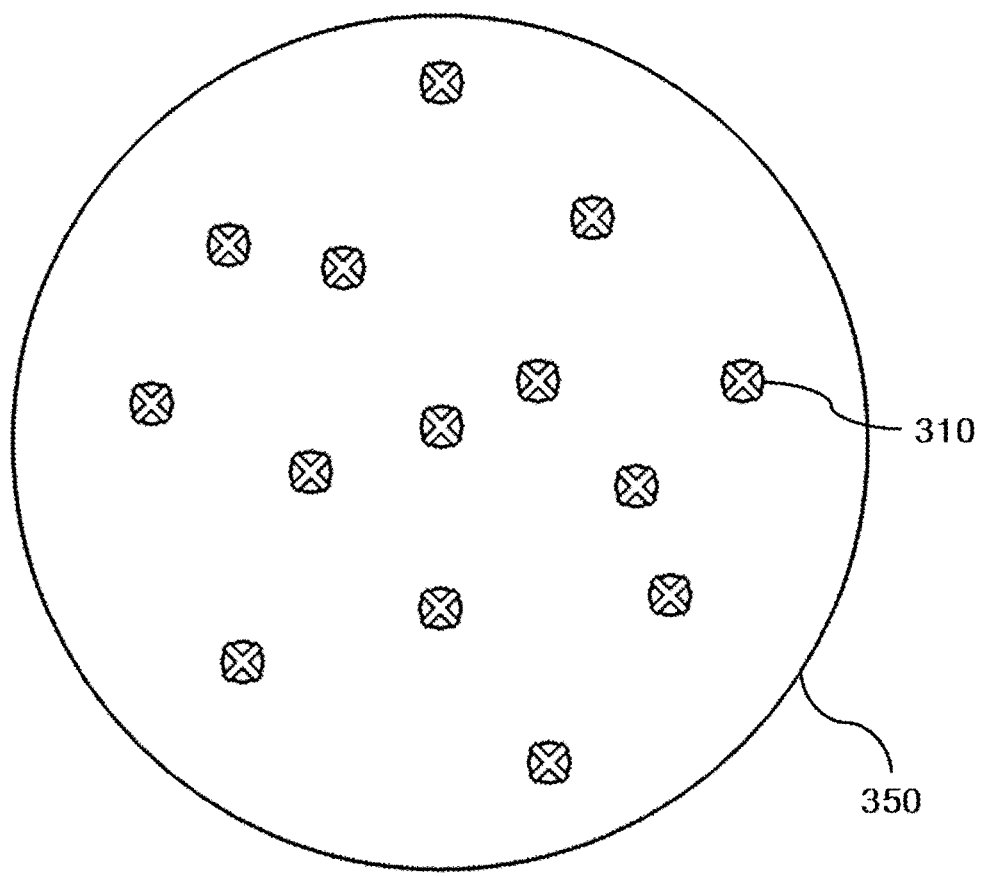

FIGS. 2 and 3 are diagrams showing a probe structure having both ultrasonic converters for obtaining an ultrasound image and HIFU converters for ultrasound treatment.

To receive feedback of the treated condition through an image simultaneously with HIFU treatment, as shown in FIG. 2, ultrasonic converters 210 for imaging are densely arranged at the center of a circular probe assembly 250 and converters 220 for HIFU treatment are disposed at the surrounding region, thereby obtaining an image simultaneously with treatment. However, the probe assembly 250 designed as described above has a smaller region formed by the image converters 210 in size than that of the HIFU converters 220. By this reason, when considering the aperture size of the probe is proportional to the resolution of the focal point, the optimum performance is not provided. That is, a small aperture of the image converters 210 causes a problem that the resolution of an ultrasound image obtained through the image converters 210 is relatively low quality. If the image converters 210 and the converters 220 for HIFU treatment are changed in position, there is a risk of another problem that the aperture of the converters 220 for HIFU treatment is smaller, making it difficult to accurately treat the lesion part of the local region.

Additionally, because the converters are arranged in divided distribution regions within one the probe assembly 250, it is unsuitable to reduce the grating lobe generated by irradiated ultrasound being focused onto an unintended region due to the gap between the converters.

In another attempt to design a probe structure having both ultrasonic converters and HIFU converters, treatment and image acquisition may be simultaneously achieved by arranging general-purpose converters 310 capable of irradiating ultrasound for both HIFU and imaging widely over the entire probe region in a circular probe assembly 350 as shown in FIG. 3.

Ultrasound for HIFU needs a lower frequency band than ultrasound for imaging when considering the penetration depth by the attenuation effect. However, when considering that the resolution of ultrasound image is proportional to the center frequency of ultrasound, in the case of ultrasound for imaging, a high frequency band is good. Accordingly, implementing ultrasound for imaging and ultrasound for HIFU using physically the same converter signifies covering two different frequency ranges, which makes the substantial converter design and implementation very difficult. Accordingly, there is a problem that the performance or efficiency reduces during use in each mode due to the feature of the general-purpose converter that is not specialized for each mode (i.e., signifying the mode for image acquisition or the mode for treatment).

Figure 4:
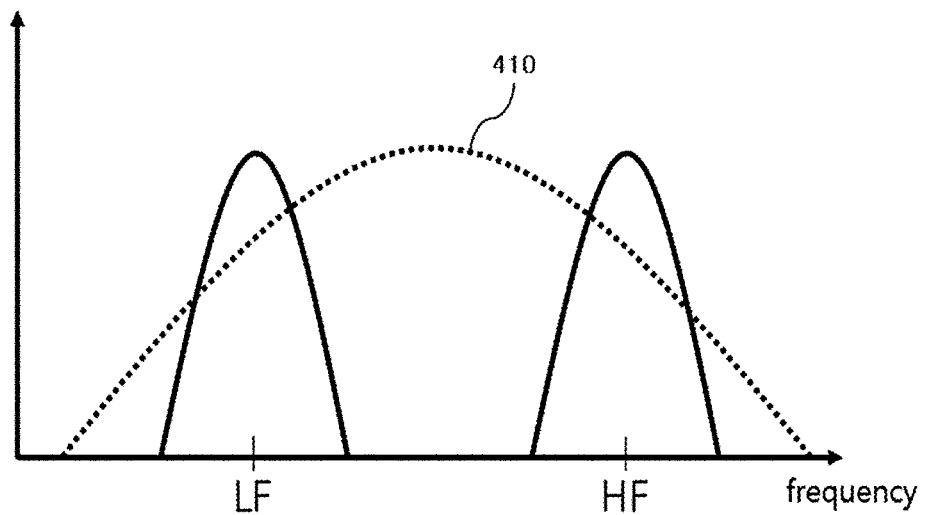
FIG. 4 is a diagram showing the frequency spectrum when transmitting two types of ultrasonic signals using the same converter of FIG. 3.

FIG. 4 is a diagram showing the frequency spectrum when transmitting two types of ultrasonic signals using the same converter of FIG. 3, and the shown graph depicts the frequency response to the center frequency. Referring to FIG. 4, it can be seen that even though both an ultrasonic signal of low frequency band and an ultrasonic signal of high frequency band are generated using physically one ultrasonic converter, its frequency response does not accurately respond to each frequency band. That is, neither low frequency band nor high frequency band is satisfied and the frequency response characteristic 410 is insensitive to a specific frequency band and occurs over the entire band, and thus a phenomenon appears in which the response performance degrades.

Accordingly, the embodiments of the present disclosure designed under the recognition of the above-described problem propose an ultrasound treatment device and its control method, in which both HIFU converters optimized for treatment and converters optimized for imaging are integrated into one probe assembly, and the individual converters are designed and arranged to suit each purpose such that efficiency is maximized, thereby necrotizing the tissue effectively in a short time and receiving feedback of the treated condition with high resolution.

Hereinafter, the embodiments of the present disclosure will be described in detail with reference to the drawings. In the drawings, the same reference number indicates the same element.

Figure 5:
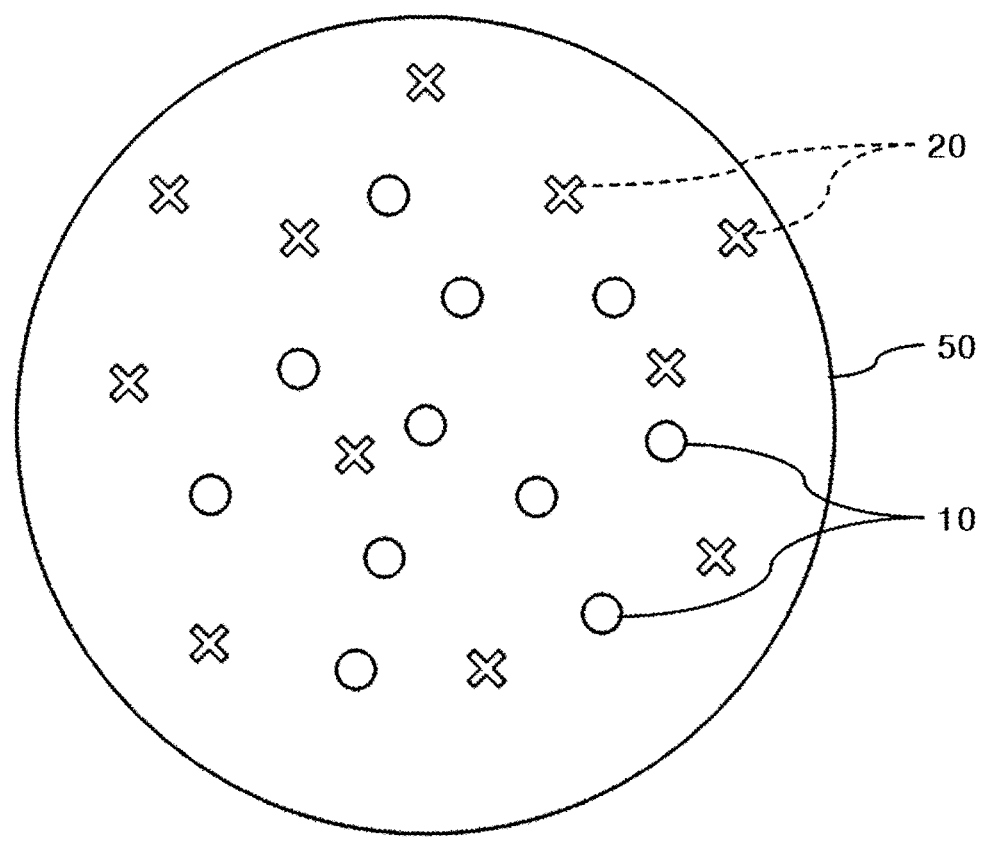
FIG. 5 is a diagram showing the schematic structure of a probe having both converters for ultrasound image and HIFU converters proposed by the embodiments of the present disclosure.

FIG. 5 is a diagram showing the schematic structure of a probe having both converters for ultrasound image and HIFU converters proposed by the embodiments of the present disclosure, and the converters 10 for ultrasound image and the converters 20 for HIFU are each manufactured to be suited for their frequency band, and arranged one surface of one the probe assembly 50 using the entire aperture of the probe without limiting a distribution area as shown in FIG. 5. In this instance, for the converter arrangement position, the converters may be freely arranged or may be optimized and arranged according to the sparse array technique.

In particular, as opposed to the probe of FIGS. 2 and 3 as previously described, the probe proposed through FIG. 5 includes a plurality of converters 10 for ultrasound image and a plurality of HIFU converters 20 for treatment over the entire region of the probe assembly 50 without distinction of a specific region, and has an advantage of maximizing the aperture of converter array formed by the driven converters upon driving the ultrasonic converters 10 for obtaining an ultrasound image or the HIFU converters 20 for treatment, respectively. Additionally, there is another advantage that it is possible to adopt converter elements having suitable frequency response characteristics for the purpose by designing and implementing the ultrasonic converters 10 and the HIFU converters 20 such that they are physically separated.

Here, the HIFU converter 20 may have the frequency response characteristic of lower center frequency band than the image converter 10, and more specifically, the image converter 10 preferably has the frequency response characteristic of the center frequency band of 3 MHz to 5 MHz, and the HIFU converter 20 preferably has the frequency response characteristic of the center frequency band of 1 MHz to 1.5 MHz.

Through the placement of the individual converters as described above, each converter 10, 20 specialized for treatment or imaging is arranged over the entire probe assembly 50, to focus ultrasound energy of low frequency band on a narrower spot, thereby necrotizing the tissue in a short time by heat (thermal ablation) and mechanical energy (cavitation), enabling noninvasive treatment of tumors or cancers. Additionally, feedback of the condition of the tissue may be received using an ultrasound image of high resolution and good quality during treatment, ensuring stability and accuracy of treatment.

Figure 6:
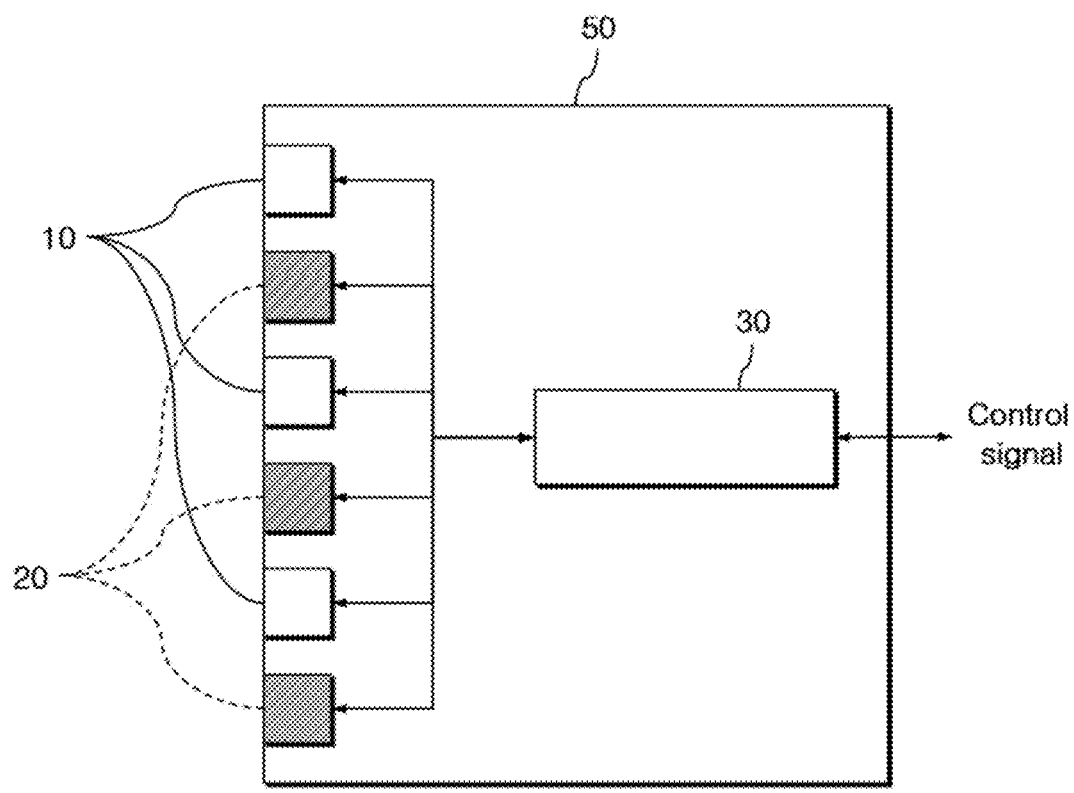
FIG. 6 is a block diagram showing an ultrasound treatment device for HIFU and ultrasound image according to an embodiment of the present disclosure.

FIG. 6 is a block diagram showing an ultrasound treatment device for HIFU and ultrasound image according to an embodiment of the present disclosure, and the probe assembly 50 may be constructed according to the converter placement method presented in FIG. 5.

The plurality of image converters 10 is configured to transmit ultrasonic signals to a target and receive the signals reflected from the target to create an ultrasound image, and the plurality of HIFU converters 20 is configured to transmit ultrasonic signals to the target to generate heat energy, thereby treating the tissue within a focusing area. The image converters 10 and the HIFU converters 20 are each disposed in physically different positions on one surface of the probe assembly 50, and they are formed to have frequency response characteristics of different center frequency bands. To this end, each converter 10, 20 may be designed and implemented as a converter element specialized for suitable frequency response characteristic for the purpose.

Additionally, the image converters 10 and the HIFU converters 20 may be each arranged randomly or in sparse array on one surface of the probe assembly 50, and as there is a risk of rendering the nature of the invention vague, a detailed description of a method for placement in sparse array is omitted herein.

Further, the image converters 10 and the HIFU converters 20 may form a circular image converter group and a circular HIFU converter group respectively by the same type of converter, and the circular image converter group and the circular HIFU converter group may be arranged to form concentric circles having different radii. The scheme for placement forming a concentric circle will be described in detail through FIGS. 9 to 12 as below.

Meanwhile, a control unit 30 is configured to generate and apply ultrasonic signals of different center frequency bands to each of the image converters 10 and the HIFU converters 20. Additionally, the control unit 30 is the means for performing control such that a difference in aperture of converter arrays constituted by the image converters 10 and the HIFU converters 20 respectively is within a predetermined value, and through this control method, it is possible to achieve the localization of the treatment region at the same time with maintaining high resolution of the ultrasound image.

Figure 7:
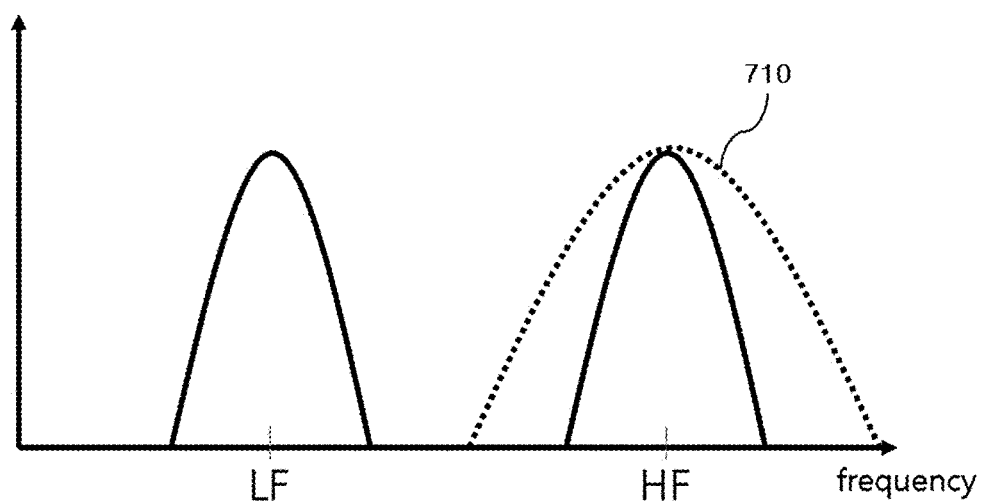
FIGS. 7 and 8 are diagrams showing the frequency response of a converter selectively specialized for the reception of ultrasound for imaging or the reception of ultrasound for treatment in obtaining an ultrasound image and performing ultrasound treatment through one probe.
Figure 8:
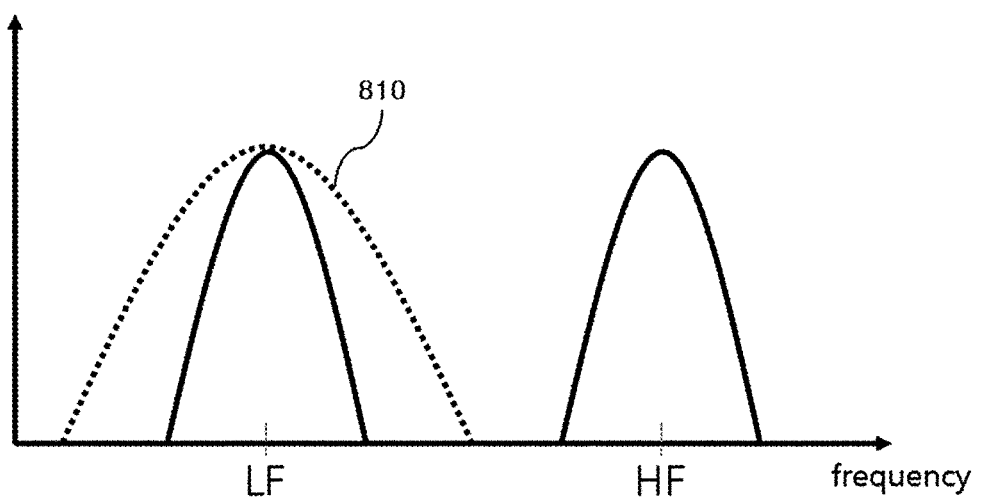

FIGS. 7 and 8 are diagrams showing the frequency response of the converter selectively specialized for the reception of ultrasound for imaging or the reception of ultrasound for treatment in obtaining an ultrasound image and performing ultrasound treatment through one probe, and they are presented to design each converter arranged in the probe assembly to have suitable frequency response for the purpose of use.

As previously described, in general, the center frequency of ultrasound for medical ultrasound imaging is 3 MHz to 5 MHz. In contrast, the center frequency of ultrasound for HIFU is about 1 MHz to 1.5 MHz. In the case of the converter, there are many variables for optimization, but a typical one is center frequency. For example, in FIGS. 7 and 8, assume LF=1 MHz, HF=3 MHz, it is physically very difficult to design the ultrasonic converter such that the frequency response satisfies both 1 MHz and 3 MHz. In contrast, it is easier to design two types of converters suited to 1 MHz and 3 MHz respectively. Accordingly, in the case of FIG. 7, the converter for imaging is designed to have the frequency response of the center frequency of 3 MHz, and in the case of FIG. 8, the converter for HIFU is designed to have the frequency response of the center frequency of 1 MHz.

That is, FIG. 7 shows a converter with a good frequency response 710 of high frequency band, and it is advantageous for this converter to be used as the image converter 10 of the ultrasound treatment device of FIG. 6 providing high quality resolution at the high frequency band. In contrast, FIG. 8 shows a converter with a good frequency response 810 of low frequency band, and it is advantageous for this converter to be used as the HIFU converter 20 of the ultrasound treatment device of FIG. 6 requiring the frequency response of low frequency band.

Hereinafter, various implementation examples of the placement scheme of ultrasonic converters that form a concentric circle on the probe assembly will be presented in detail. To this end, the premise is that image converters and HIFU converters form a circular image converter group and a circular HIFU converter group respectively by the same type of converter to form concentric circles having different radii on one surface of the probe assembly. Additionally, from the perspective of implementation, the circular image converter group and the circular HIFU converter group are repeatedly arranged in an alternating manner in a direction in which the radius increases from the center of the probe assembly, keeping the aperture of the converter array used for image acquisition or HIFU treatment similar.

Figure 9:
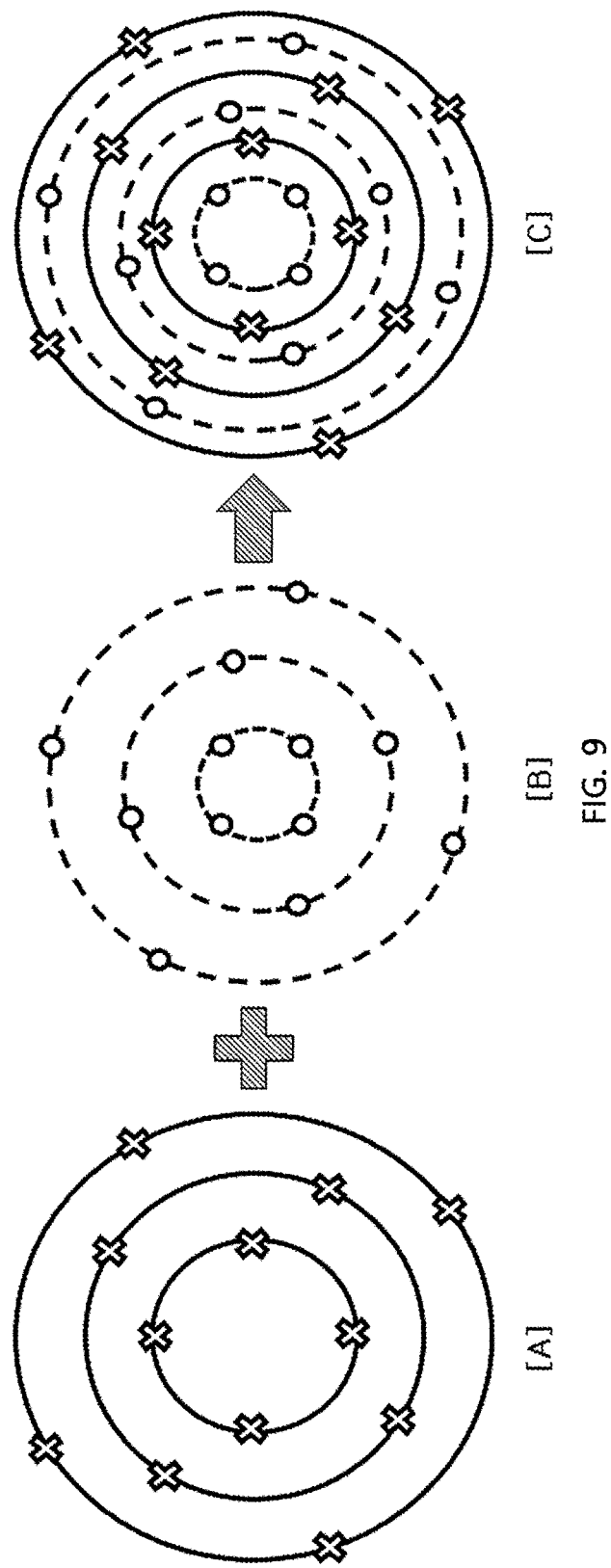
FIG. 9 is a diagram showing an example of a process of arranging converters for ultrasound image and HIFU converters in an ultrasound treatment device according to another embodiment of the present disclosure.

FIG. 9 is a diagram showing an example of a process of optimizing and arranging converters for ultrasound image and HIFU converters in an ultrasound treatment device according to another embodiment of the present disclosure. As shown in FIG. 9, a converter group including a plurality of circular array converters is formed, and each converter group is composed of only one type of converters. That is, a circular array converter is formed by only one of converter group [B] for imaging and converter group [A] for treatment. Subsequently, after each of the converter group [B] for imaging and the converter group [A] treatment is optimized with regard to converter placement, these converter groups are arranged in an alternating manner forming a concentric circle, like [C] on one probe assembly.

If necessary, the image converters included in the circular image converter group and the HIFU converters included in the circular HIFU converter group may be arranged at the same interval on each concentric circle. In this instance, when a virtual baseline going through the center of the circle is assumed, it is desirable to randomly arrange the first converters of each converter group to minimize the influence of the grating lobe or side lobe generated by the gap between the converters. That is, it is advantageous that the converters belonging in different groups on the virtual baseline are not arranged side by side in a line.

Figure 10:
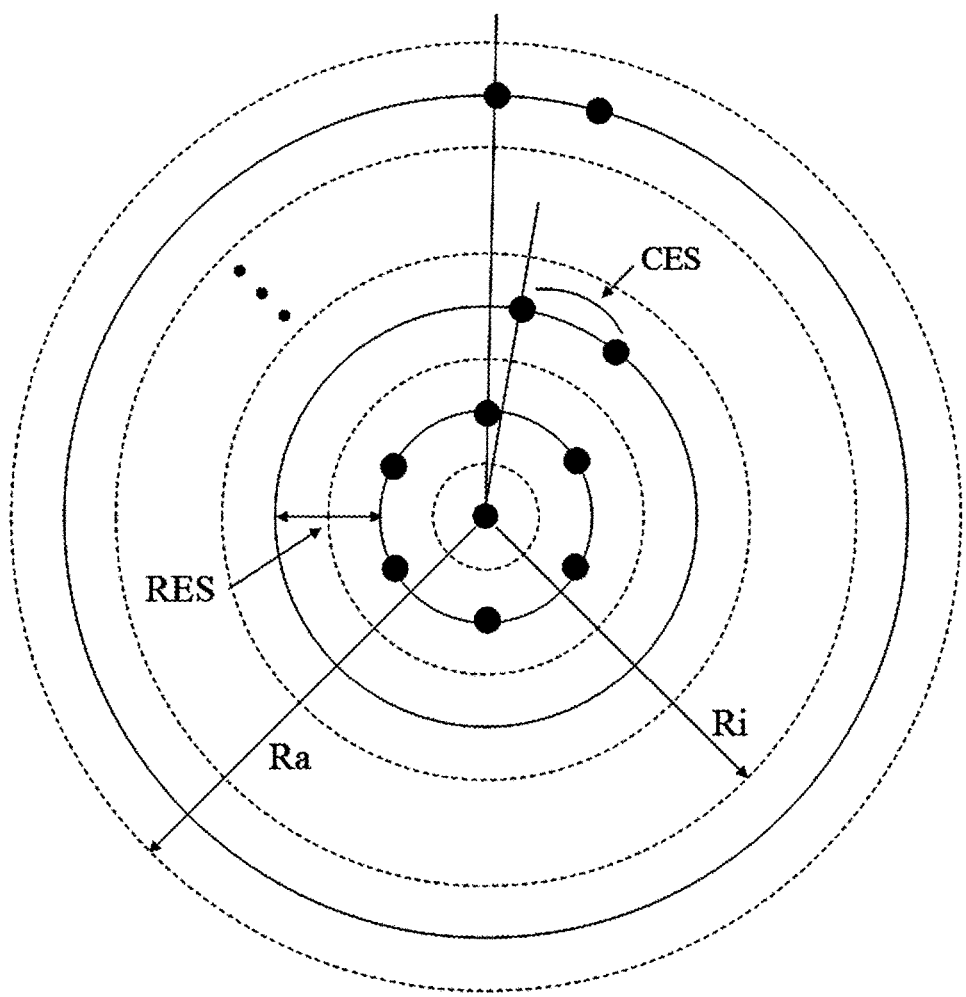
FIGS. 10 to 12 are diagrams showing the scheme of determining the size of a circular converter formed by each of the converters for ultrasound image and the HIFU converters in the ultrasound treatment device of FIG. 9 according to another embodiment of the present disclosure.
Figure 11:
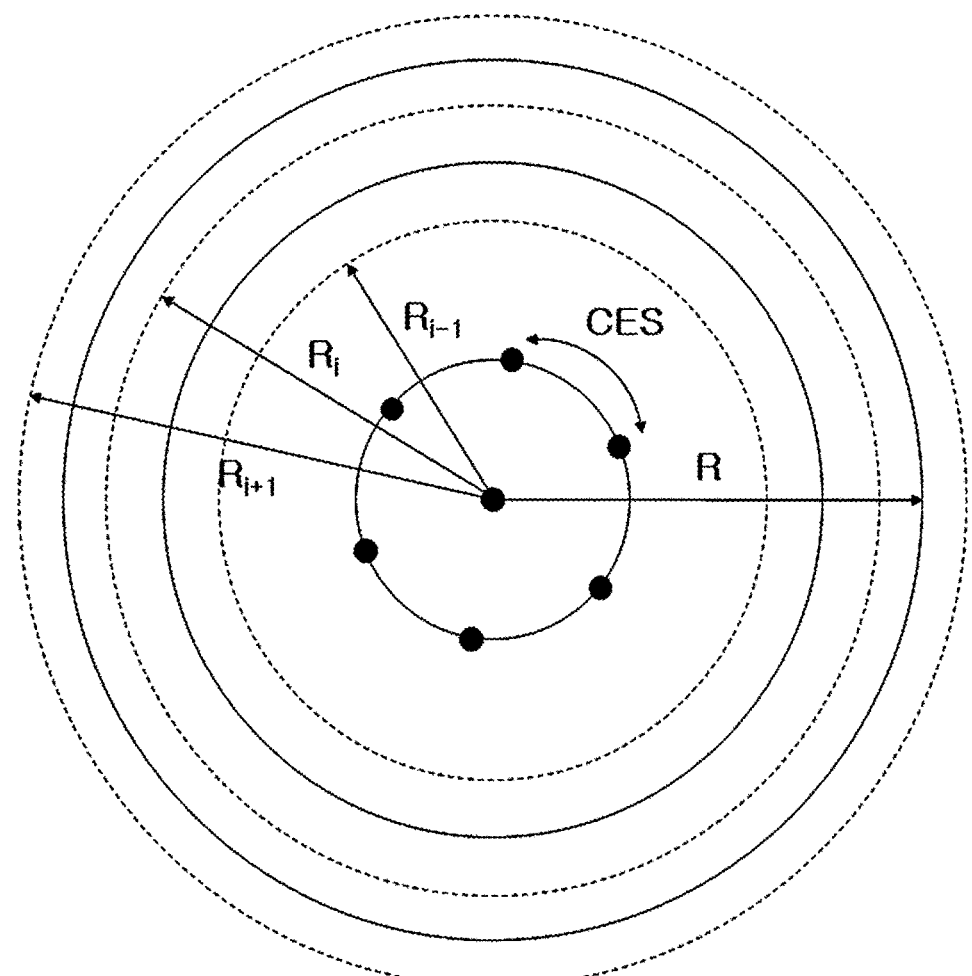
Figure 12:
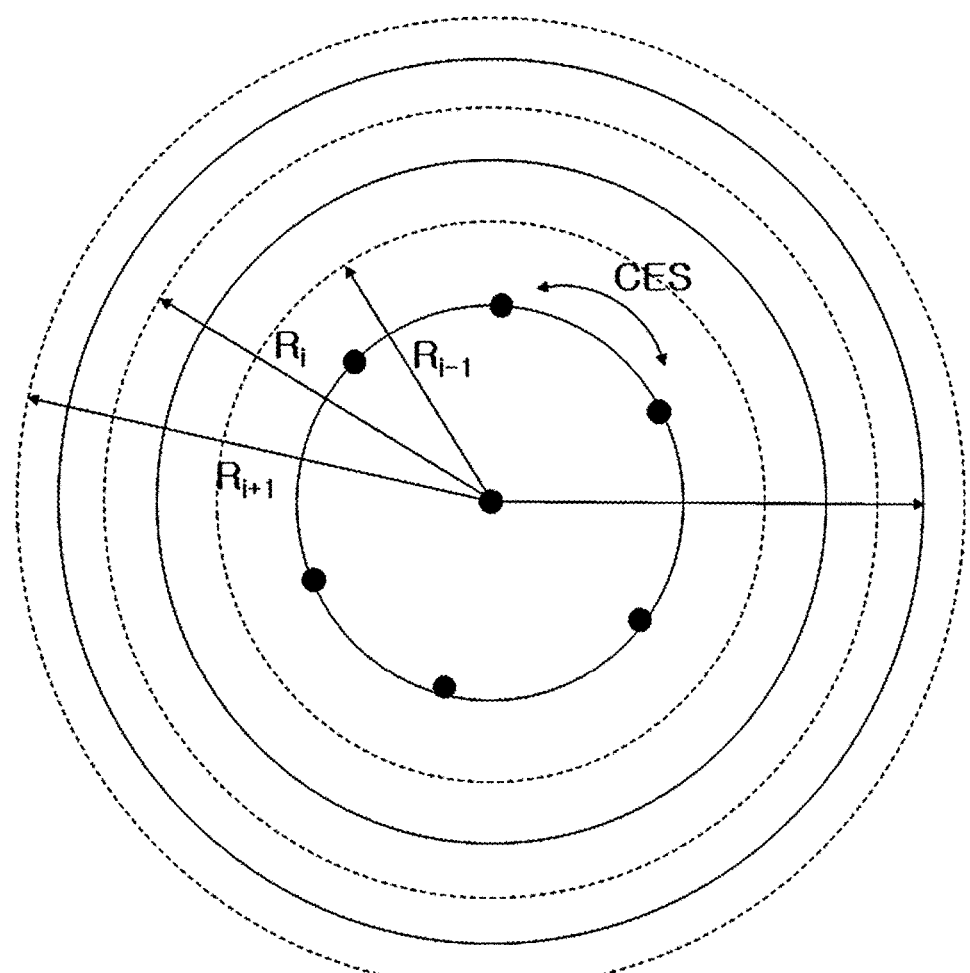

FIGS. 10 to 12 are diagrams showing the scheme of determining the size of the circular converter formed by each of the converters for ultrasound image and the HIFU converters in the ultrasound treatment device of FIG. 9 according to another embodiment of the present disclosure. Here, the solid line indicates a concentric circle in which the circular image converter group or the circular HIFU converter group may be actually disposed, and the dash line is an auxiliary line for determining the placement of the converter group and is represented as a virtual concentric circle. The placement scheme according to FIGS. 10 to 12 may be individually applied to both the circular image converter group and the circular HIFU converter group, and here, the placement scheme of placing only one type of converter irrespective of the type of converter is introduced, and it can be seen that the converter placement structure as previously described through FIG. 9 may be completed by overlapping the concentric circle structures disposed for each type of converter.

First, referring to FIG. 10, in placing the circular converter group on one probe assembly forming a concentric circle, the concentric circles may be arranged at the same interval on the solid lines. That is, in FIG. 10, each converter group may be arranged at the same distance as adjacent converter groups (signifying that the Radial Equal Spacing (RES) values are equal to each other) on the basis of the center of the circular converter. Additionally, as illustrated, individual converters that form the converter group may be also arranged at the same distance as adjacent converters (signifying that the Circumferential Equal Spacing (CES) values are equal to each other). Accordingly, the dash line of FIG. 10 is represented as a virtual concentric circle spaced the same distance apart from an adjacent solid line, and actually represents an auxiliary line that is irrelevant to the converter placement.

Second, referring to FIG. 11, in placing the circular converter group on one probe assembly forming a concentric circle, the radii of at least two virtual concentric circles (unless the origin of the concentric circle is included, three virtual concentric circles) (indicated by the dash line) may be determined such that the area of each region separated by the at least two virtual concentric circles is equal, a new concentric circle (a location at which the converters are actually disposed, indicated by the solid line) may be formed on the basis of an average of radii of adjacent virtual concentric circles of the virtual concentric circles, and any one of the circular image converter group and the circular HIFU converter group may be arranged on the formed new concentric circle. This placement scheme is a method that places the converter group (indicated by the solid line) corresponding to the new concentric circle in between the radii at which the area of each region separated by the concentric circles is equal.

As illustrated in FIG. 11, when three virtual concentric circles are $R_{i-1}$, $R_i$, $R_{i+1}$ in a sequential order from a small radius value, the radius at which the area of each region is equal has a relationship of Equation 1.

$$R_{i+1}^2 - R_i^2 = R_i^2 - R_{i-1}^2 \qquad \text{[Equation 1]}$$

In Equation 1, assume that i is a positive integer, and $R_0=0$. Accordingly, among three virtual concentric circles intended to find according to Equation 1, a concentric circle formed at the innermost becomes the center of a circle whose radius is 0, and actually only two virtual concentric circles remain.

That is, when the length between adjacent radii is determined by the above-described relationship, a circular converter group (indicated by the solid line) may be disposed with respect to a new concentric circle whose radius is the length corresponding to an average of two radii of adjacent virtual concentric circles (indicated by the dash line). Also, in this case, as illustrated, individual converters that form the converter group may be arranged at the same distance as adjacent converters (signifying that the CES values are equal to each other).

Third, referring to FIG. 12, in placing the circular converter group on one probe assembly forming a concentric circle, the radii of at least two virtual concentric circles (indicated by the dash line) may be determined such that the area of each region separated by the virtual concentric circles is equal, a new concentric circle (a location at which the converters are actually disposed, indicated by the solid line) may be formed at a location where the area of each region separated by the virtual concentric circles is divided into two, and any one of the circular image converter group and the circular HIFU converter group may be arranged on the formed new concentric circle. This placement scheme is a method that finds a radius at which the area of each region separated by the concentric circles is equal, and places the converter group (indicated by the solid line) corresponding to the new concentric circle at a location where the region is divided into two of equal areas again.

That is, the method of FIG. 12 is performed in the same way until the process of initially determining the position of virtual concentric circles using Equation 1 according to the method of FIG. 11 as previously described. However, they differ in a method for finding a location at which the circular converter group is actually disposed between adjacent virtual concentric circles (indicated by the solid line) afterwards, and there is a difference in that the distance is divided into two of equal areas, not equal intervals as shown in FIG. 11. Of course, also in this case, individual converters that form the converter group may be arranged at the same distance as adjacent converters (signifying that CES values are equal to each other) as illustrated.

Figure 13:
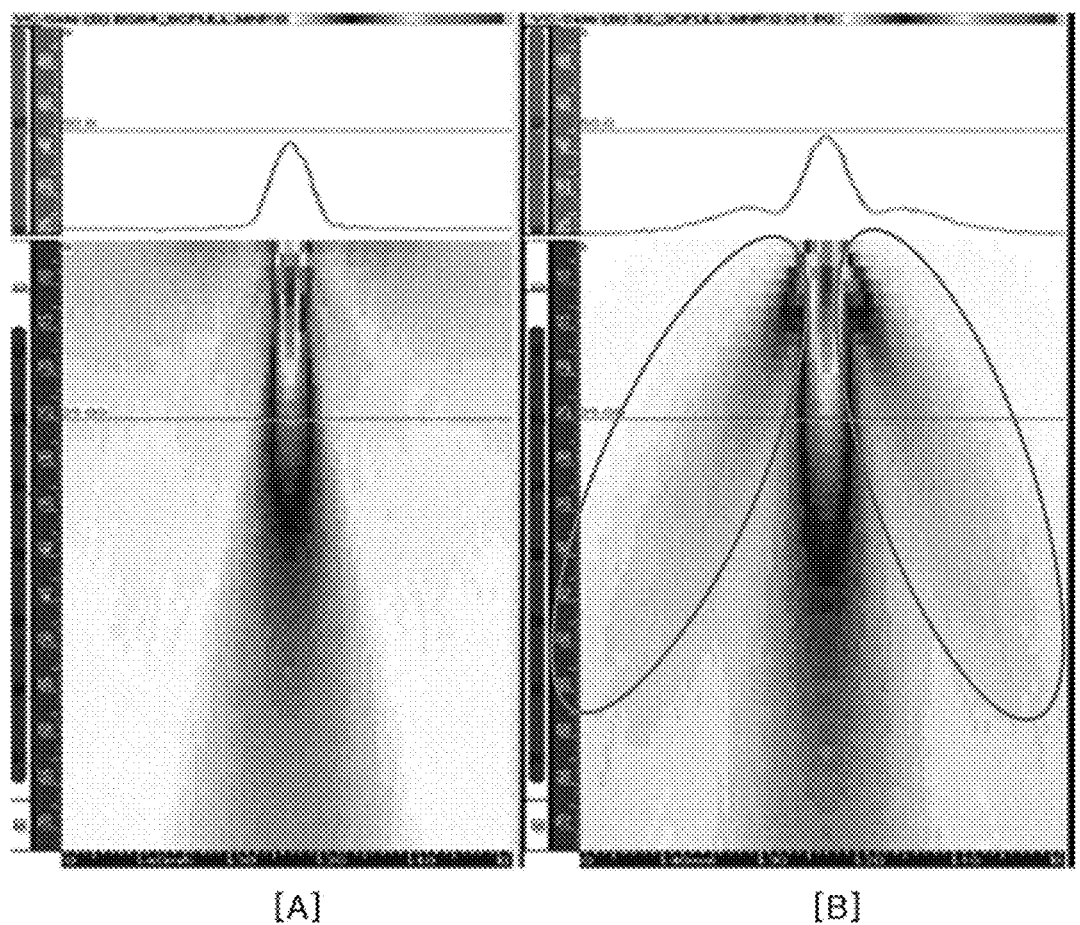
FIG. 13 is a diagram illustrating the grating lobe according to ultrasonic converter placement.

FIG. 13 is a diagram illustrating the grating lobe according to ultrasonic converter placement.

In general, when converters are regularly arranged, there is a likelihood that the grating lobe may be generated by irradiated ultrasound being focused on an unintended area due to the gap between the converters. From FIG. 13, it can be seen that in [A], only the main lobe is formed, whereas in [B], grating lobes are formed at two sides of the main lobe. Accordingly, in arranging the converters on the probe assembly, it is important to adopt a scheme by which the converters are arranged randomly and sparsely (not densely).

However, from the perspective of substantial implementation, randomly arranging converters may make it difficult to manufacture, or rather may generate the side lobe. Accordingly, when following the placement scheme of FIGS. 9 to 12 in terms of ease of manufacture, it is possible to produce a probe assembly with consistent feature and predictable pattern of beam formation.

Figure 14:
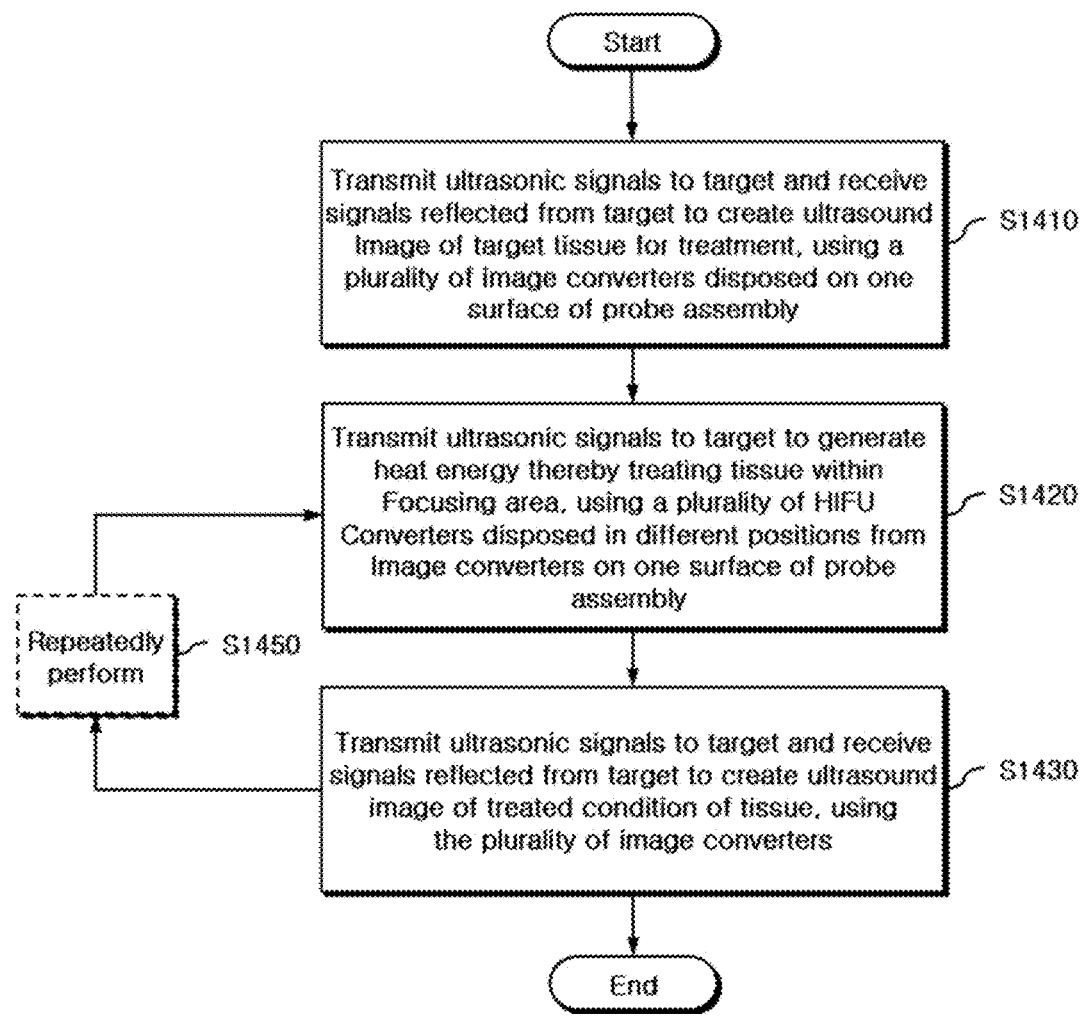
FIG. 14 is a flowchart showing a control method for an ultrasound treatment device according to still another embodiment of the present disclosure.

FIG. 14 is a flowchart showing a control method for an ultrasound treatment device according to still another embodiment of the present disclosure, and proposes a series of steps of controlling the ultrasound treatment device according to the configuration of FIG. 6 as previously described to suit the purpose from the time-series perspective, and here, the individual configuration of the probe assembly will be described in brief to avoid the overlap of description.

In S1410, the ultrasound treatment device transmits ultrasonic signals to a target and receives the signals reflected from the target to create an ultrasound image of the target tissue for treatment, using a plurality of image converters disposed on one surface of the probe assembly.

In S1420, the ultrasound treatment device transmits ultrasonic signals to the target to generate heat energy, thereby treating the tissue within a focusing area, using a plurality of HIFU converters disposed in different positions from the image converters on one surface of the probe assembly.

In S1430, the ultrasound treatment device transmits ultrasonic signals to the target and receives the signals reflected from the target to create an ultrasound image of the treated condition of the tissue, using the plurality of image converters. This process is a process for identifying the effects of treatment, and S1420 and S1430 are performed repeatedly at least once by controlling each of the image converters and the HIFU converters, as in S1450, according to the determination/decision of the generated result image. That is, HIFU treatment and image monitoring may be repeated until the effects of treatment reach the satisfactory level.

Additionally, the image converters and the HIFU converters may be each arranged randomly or in sparse array on one surface of the probe assembly, and in S1410 to S1430, the image converters and the HIFU converters may be each selectively driven, and the aperture of the converter array may be determined by the driven converters.

Additionally, the image converters and the HIFU converters may form a circular image converter group and a circular HIFU converter group respectively by the same type of converter, and the circular image converter group and the circular HIFU converter group may be arranged to form concentric circles having different radii, and in S1410 to S1430, the image converters and the HIFU converters may be each selectively driven, and the aperture of the converter array may be determined by the diameter of the driven converter group.

Additionally, in S1410 to S1430, among the image converters included in the circular image converter group and the HIFU converters included in the circular HIFU converter group, the converters arranged at the same interval on each concentric circle may be selectively driven.

Additionally, in S1410 to S1430, the circular image converter group and the circular HIFU converter group arranged repeatedly in an alternating manner in a direction in which the radius increases form the center of the probe assembly may be selectively driven, and it is preferred to perform control such that a difference in aperture of the driven converter group is within a predetermined value. Through this configuration, high resolution achievement of ultrasound image acquisition and localization of HIFU treatment may be simultaneously enabled.

Additionally, in S1410 to S1430, it is preferred to selectively drive each converter disposed at a location where the influence of the grating lobe generated by the gap between the converters is minimized.

Further, the HIFU converters have the frequency response characteristic of lower center frequency band than the image converters, and in S1410 to S1430, ultrasonic signals of different center frequency bands may be generated and applied to each of the image converters and the HIFU converters.

The present disclosure has been hereinabove described with regard to its various embodiments. Those having ordinary skill in the technical field pertaining to the present disclosure will understand that the present disclosure may be embodied in modified form without departing from the essential feature of the present disclosure. Therefore, the disclosed embodiments are meant to be illustrative, not limiting in scope. The scope of the present disclosure is defined by the appended claims rather than the foregoing description, and it should be interpreted that the present disclosure covers all changes made within its equivalent scope.

INDUSTRIAL APPLICABILITY

According to the above-described embodiments of the present disclosure, two types of converters for different purposes of uses are not distributed in different regions or limited regions within the probe assembly and they are arranged all over one surface of the probe, thereby realizing a large aperture of each converter, so that ultrasound may be focused on a narrow area. Accordingly, an image of good resolution in lateral direction may be fed back, and with the placement technique for minimizing the influence of the grating lobe, it is possible to prevent ultrasound from being focused on regions other than the focusing area. Accordingly, energy may be concentrated on only a target local part for treatment without damaging normal tissues around the lesion part. As a result, only the lesion tissue may be necrotized in a short time, and thus it is possible to solve the temperature rise problem on the skin surface over time that arises when performing high intensity focused ultrasound (HIFU) treatment.

Additionally, because the converters having suitable frequency response for each purpose are used, the attenuation effect of signals may be reduced by performing treatment with low frequency band, and one of HIFU effects, mechanical energy (cavitation), may be generated more effectively, thereby improving the effects of treatment. Besides, images of good axial direction resolution may be obtained by irradiation of ultrasound for imaging with high frequency band, so the condition of the tissue may be accurately determined, thereby increasing the accuracy of treatment.

The invention claimed is:

1. An ultrasound treatment device comprising:
    a plurality of image converters configured to transmit ultrasound signals to a target and receive the signals reflected from the target to create an ultrasound image; and
    a plurality of high intensity focused ultrasound (HIFU) converters configured to transmit ultrasound signals to the target to generate heat energy, thereby treating the tissue within a focusing area; and
    wherein the ultrasound treatment device is configured to determine an aperture of an IC array of the plurality of image converters, determine an aperture of an HIFU array of the plurality of HIFU converters, and selectively drive each of the IC array and the HIFU array such that a difference in the apertures of the IC array and the HIFU array is within a predetermined value,
    wherein the image converters and the HIFU converters are each disposed in different positions across one surface of the probe assembly, and are of different converter types formed to have frequency response characteristics of different center frequency bands.

2. The ultrasound treatment device according to claim 1, wherein the HIFU converters have frequency response characteristic of lower center frequency band than the image converters and the image converters and HIFU converters are configured to operate to obtain feedback of a treated condition through an image simultaneously with HIFU treatment.

3. The ultrasound treatment device according to claim 2, wherein the image converters have frequency response characteristic of a center frequency band of 3 MHz to 5 MHz, and
    the HIFU converters have frequency response characteristic of a center frequency band of 1 MHz to 1.5 MHz.

4. The ultrasound treatment device according to claim 1, wherein the image converters and the HIFU converters are each arranged randomly or in sparse array on one surface of the probe assembly.

5. The ultrasound treatment device according to claim 1, wherein the image converters and the HIFU converters form a circular image converter group and a circular HIFU converter group respectively by the same type of converter, and the circular image converter group and the circular HIFU converter group are arranged to form concentric circles having different radii.

6. The ultrasound treatment device according to claim 1, further configured to control the image converters and the HIFU converters to generate and apply ultrasonic signals of different center frequency bands, respectively.

7. An ultrasound treatment device comprising:
    a plurality of image converters positioned on a probe assembly and configured to transmit ultrasonic signals to a target and receive the signals reflected from the target to create an ultrasound image; and
    a plurality of high intensity focused ultrasound (HIFU) converters positioned on the probe assembly and configured to transmit ultrasonic signals to the target to generate heat energy, thereby treating the tissue within a focusing area,
    wherein the plurality of image converters are spaced from each other and arranged across one surface of the probe assembly in a first circle to form a circular image converter group and the plurality of HIFU converters are spaced from each other and arranged on the one surface of the probe assembly in a second circle to form a circular HIFU converter group such that the first and second circles form concentric circles having different radii, wherein the image converters included in the circular image converter group and the HIFU converters included in the circular HIFU converter group are arranged at the same interval on each concentric circle, and wherein each of the plurality of image converters in the circular image converter group and each of the plurality of HIFU converters in the circular HIFU converter group are randomly arranged such that each of the plurality of image converters are offset from being side by side in a line with any of the plurality of HIFU converters.

8. The ultrasound treatment device according to claim 7, wherein the image converters included in the circular image converter group and the HIFU converters included in the circular HIFU converter group are disposed at a location where the influence of grating lobe generated by a gap between the converters is minimized.

9. The ultrasound treatment device according to claim 7, wherein the circular image converter group and the circular HIFU converter group are repeatedly arranged in an alternating manner in a direction in which the radius increases from a center of the probe assembly and the plurality of image converters and the plurality of HIFU converters are configured to operate to obtain feedback of a treated condition through an image simultaneously with HIFU treatment.

10. The ultrasound treatment device according to claim 7, wherein the circular image converter group and the circular HIFU converter group are arranged such that adjacent concentric circles have the same interval.

11. The ultrasound treatment device according to claim 7, wherein the radii of at least two virtual concentric circles are determined such that the area of each region separated by the at least two virtual concentric circles is equal, a new concentric circle is formed on the basis of an average of radii of adjacent virtual concentric circles of the at least two virtual concentric circles, and any one of the circular image converter group and the circular HIFU converter group is disposed on the formed new concentric circle.

12. The ultrasound treatment device according to claim 7, wherein the radii of at least two virtual concentric circles are determined such that the area of each region separated by the virtual concentric circles is equal, a new concentric circle is formed at a location where the area of each region separated by the virtual concentric circles is divided into two, and any one of the circular image converter group and the circular HIFU converter group is disposed on the formed new concentric circle.

13. A control method for an ultrasound treatment device, comprising:

(a) transmitting ultrasonic signals to a target and receiving the signals reflected from the target to create an ultrasound image of a target tissue for treatment, using a plurality of image converters disposed across one surface of a probe assembly;

(b) transmitting ultrasonic signals to the target to generate heat energy, thereby treating the tissue within a focusing area, using a plurality of high intensity focused ultrasound (HIFU) converters disposed in different positions from the image converters on one surface of the probe assembly; and (c) transmitting ultrasonic signals to the target and receiving the signals reflected from the target to create an ultrasound image of the treated condition of the tissue, using the plurality of image converters, wherein the steps (b) and (c) are repeatedly performed at least once by controlling each of the image converters and the HIFU converters and the plurality of image converters and the plurality of HIFU converters are of different converter types;

(d) maintaining an aperture difference, comprising:

determining an aperture of an IC array of the plurality of image converters;

determining an aperture of an HIFU array of the plurality of HIFU converters; and selectively driving each of the IC array and the HIFU array such that a difference in the apertures of the IC array and the HIFU array is within a predetermined value.

14. The control method for an ultrasound treatment device according to claim 13, wherein the image converters and the HIFU converters are each arranged randomly or in sparse array on one surface of the probe assembly, and the steps (a) to (c) include selectively driving each of the image converters and the HIFU converters, and determining the aperture of the IC array and the HIFU array by the driven converters.

15. The control method for an ultrasound treatment device according to claim 13, wherein the image converters and the HIFU converters form a circular image converter group and a circular HIFU converter group respectively by the same type of converter, and the circular image converter group and the circular HIFU converter group are arranged to form concentric circles having different radii, and the steps (a) to (c) include selectively driving each of the image converters and the HIFU converters, and determining the aperture of the IC array and the HIFU array by the diameter of the driven converter group.

16. The control method for an ultrasound treatment device according to claim 15, wherein the steps (a) to (c) include selectively driving converters arranged at the same interval on each concentric circle among the image converters included in the circular image converter group and the HIFU converters included in the circular HIFU converter group.

17. The control method for an ultrasound treatment device according to claim 15, wherein the steps (a) to (c) include selectively driving the circular image converter group and the circular HIFU converter group repeatedly arranged in an alternating manner in a direction in which the radius increases from a center of the probe assembly.

18. The control method for an ultrasound treatment device according to claim 13, wherein the steps (a) to (c) include selectively driving each converter disposed at a location where the influence of grating lobe generated by a gap between the converters is minimized.

19. The control method for an ultrasound treatment device according to claim 13, wherein the HIFU converters have frequency response characteristic of lower center frequency band than the image converters, and the steps (a) to (c) are performed concurrently and include generating and applying ultrasonic signals of different center frequency bands to each of the image converters and the HIFU converters to obtain feedback of a treated condition through an image simultaneously with HIFU treatment.

20. The ultrasound treatment device according to claim 7, wherein the image converters included in the circular image converter group and the HIFU converters included in the circular HIFU converter group are of different converter types.

\* \* \* \* \*